United States Patent [19]

Taylor

[11] 4,250,998
[45] Feb. 17, 1981

[54] DIABETIC TRAVEL KIT

[75] Inventor: Frank Taylor, 9415 Central St., LaSalle, Quebec, Canada, H8R 2K4

[73] Assignee: Frank Taylor, LaSalle, Canada

[21] Appl. No.: 63,733

[22] Filed: Aug. 6, 1979

[51] Int. Cl.³ .................... B65D 81/38; B65D 81/18; F25D 3/08
[52] U.S. Cl. ............................ 206/570; 206/571; 220/428; 62/371
[58] Field of Search .............. 206/570, 232, 803; 220/428, 23; 62/371, 372

[56] References Cited

U.S. PATENT DOCUMENTS

| 1,525,858 | 2/1925 | Farrell, Jr. | 206/803 |
| 2,410,928 | 11/1946 | Christner et al. | 206/232 |
| 2,724,494 | 11/1955 | Graff | 220/428 |
| 2,738,890 | 3/1956 | Dahl et al. | 220/428 |
| 2,740,516 | 4/1956 | Renn | 206/803 |
| 3,413,820 | 12/1968 | Paquin | 220/428 |

Primary Examiner—William T. Dixson, Jr.

[57] ABSTRACT

A diabetic travel kit is formed by an insulated container having a cavity in which is received a cooling medium container having an annular cooling medium chamber surrounding a top opening compartment. An insulated lid closes the cavity. Preferably top opening pockets are formed in the peripheral walls of the insulated container, and the lid is provided with means to close the pockets when the lid is in place closing the cavity.

5 Claims, 6 Drawing Figures

U.S. Patent  Feb. 17, 1981  4,250,998
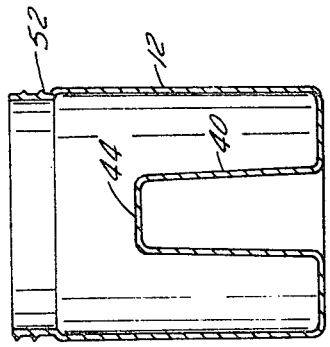
FIG. 3
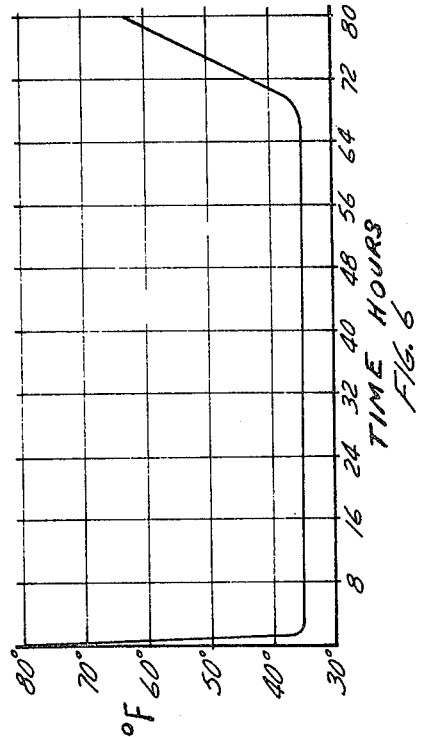
FIG. 6
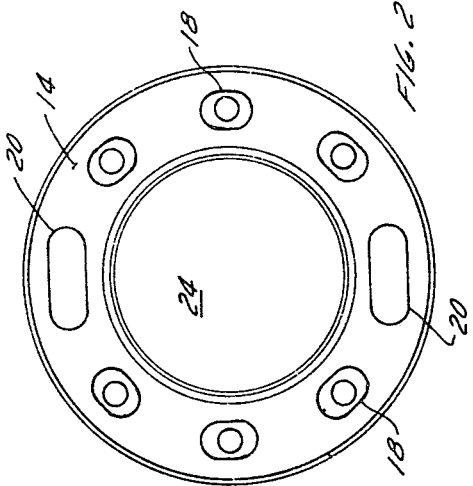
FIG. 2
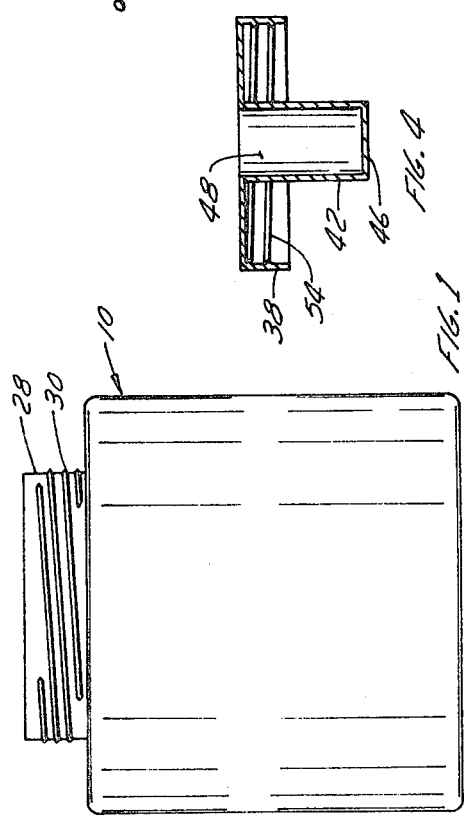
FIG. 4
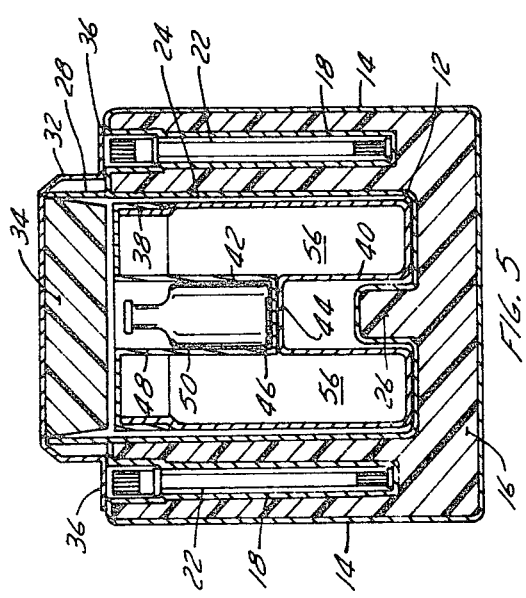
FIG. 5
FIG. 1

DIABETIC TRAVEL KIT

FIELD OF THE INVENTION

This invention consists of a portable cooler, more specifically the present invention relates to a cooler for the transportation of insulin and other items related to the use of insulin, by persons who suffer from diabetes, or as it may be more appropriately called, a diabetic travel kit.

BACKGROUND OF THE INVENTION

Insulin is an extract from the pancreas of certain animals which is mixed with other chemicals to form a liquid preparation and is generally marketed in small vials or bottles containing 10 cc's of the fluid. Insulin has been sold in three main concentrations, namely, U-40, U-80 and U-100. The difference is in how much liquid volume the preparation contains for each unit of insulin, or how pure the preparation is in terms of insulin. With U-100 preparations, a single cc of the liquid contains 100 units of insulin, while with the U-80, that same amount of liquid contains only 80 units of insulin, and with U-40, only 40 units. In the United States and Canada, however, insulin preparations containing 40 units per cc or 80 units per cc are being replaced by preparations containing 100 units per cc. This applies to all the various forms of insulin preparations. The diabetic travel kit herein described, therefore, is intended for use with U-100 preparations of insulin but can be adapted for other preparations.

According to the recommendations of the manufacturers of insulin, the preparation should be kept in a cold place, preferably a referigerator when stored, and at a temperature of 35 to 50 degrees F. Insulin which is in use should be kept from extreme heat, freezing temperatures and strong light. In normal use insulin is quite stable and may be kept at room temperature for some time without deterioration.

If a diabetic, however, is to lead a "normal" life as he or she would, and travelling becomes a part of this "normal" life, there are times and circumstances during which the diabetic is not able to preserve his or her insulin supply under optimum conditions, or even room temperatures. For example, if a diabetic is travelling by car on a trip of two or three days duration, or even a shorter time for that matter, the insulin, particularly if carried in the trunk of the car, may be subject to temperatures considerably higher than "room temperature", conceivably 50 or 60 degrees F higher. Similarly, when camping, hiking, or fishing, the insulin carried by a diabetic could, in many instances, be subject to much higher than normal temperatures and, being an animal product, adversely affected by such temperature, resulting in loss of potency or spoilage.

Another factor that may influence the diabetic may be purely psychological and this is the "peace-of-mind" factor which the device may provide to the diabetic. Since personal health or well being is, or should be, paramount in the mind of the diabetic, the condition of the life-preserving insulin is of utmost importance to the diabetic who may be away from family, friends or physician. Since concern or worry produces stress and stress in turn can adversely affect the blood-sugar level of the diabetic, it is important for the diabetic who is travelling not to be concerned about having ready access to insulin known to be preserved at the optimum temperature at all times.

BRIEF DESCRIPTION OF THE INVENTION

It is the main object of the present invention therefor, is to provide an efficient, low-cost means of transporting a vial of insulin in a small enclosure while keeping the temperature of such insulin in the optimum temperature range of 35 to 50 degrees F. for a prolonged period of time, such as two or three days.

Another object of the present invention is to provide in such a device, storage space for an appropriate number of disposable syringes and alcohol swabs necessary to the injection procedure.

Broadly, the present invention comprises an outer container having insulated peripheral and bottom walls defining a cavity, an insulated lid for closing said cavity, an inner container adapted to be received within said cavity, a top closure for said inner container, said inner container and said top closure combining when said top is in place on said inner container to form a substantially annular closed cooling medium chamber surrounding an inner central pillar providing a top opening compartment adapted to receive material for storage. In the preferred arrangement, the insulated peripheral walls are formed with pockets and the lid preferably closes said pockets and is removable to permit access to said inner container and said discrete compartments.

BRIEF DESCRIPTION OF THE DRAWINGS

Further features, objects and advantages will be evident from the following detailed description of the preferred embodiments of the present invention taken in conjunction with the accompanying drawings, in which;

FIG. 1 is a side elevation view of the insulated outer container.

FIG. 2 is a plan view of the container of FIG. 1.

FIG. 3 is a radial section through an inner container for the outer container of FIGS. 1 and 2.

FIG. 4 is a radial section through a lid for the inner container of FIG. 3.

FIG. 5 is a radial section through the combined container showing the insulated lid on the outer container also closing pockets in the peripheral wall of the container.

FIG. 6 is a time/temperature curve indicating insulin temperature over a three day period, stored using one embodiment of the present invention.

DESCRIPTION OF THE PREFERRED EMBODIMENTS

The present invention is composed of an outer insulated container 10 (FIGS. 1 and 2) adapted to telescopingly receive an inner container 12.

The outer container 10 is provided with an insulated peripheral wall 14 (see FIGS. 2 and 5) which in the illustrated arrangement is substantially cylindrical and an insulated bottom wall 16 (see FIG. 5). The peripheral wall 14 is provided with a plurality of discrete pockets as indicated by the reference numerals 18 and 20. The pockets 18 are adapted to removably receive and safely store disposable syringes as indicated at 22 in FIG. 5, while the pockets 20 are sized to conveniently contain swabs (not shown).

The walls 14 and 16 define a cavity 24 into which the inner container 12 may be inserted. An axial projection 26 extends into the cavity 24. An upwardly extending flange 28 forms the mouth of the cavity 24 and is provided with means such as threads 30 to engage mating threads or the like on the top closure or lid 32 to permit the top closure 32 to be secured in position on the outer container 10.

The lid 32 is insulated as indicated at 34 over the area covering the mouth of the cavity 24 and is provided with an outwardly extending peripheral flange 36 at its lower most edge. The flange 36 is adapted to be forced down onto the top of the wall 14 and close the pockets 18 and 20 to seal the contents thereof in place (see FIG. 5).

The inner container 12 is a coolant container and is provided with a top closure 38. The container 12 and closure 38 are provided with upwardly extending and downwardly extending pillars 40 and 42 respectively in axial alignment when the container 12 is closed and of substantially the same outside dimensions with their extremities 44 (top) and 46 (bottom) adapted to be in substantially face-to-face contact when the lid 38 is secured in position on the container 12 (see FIG. 5). The pillar 42 provides a compartment 48 opening toward the top of the container and sized to receive an insulin bottle 50 and the pillar 40 nests on the projection 26.

The lid 38 is secured to the top of the container 12 by suitable mating screw threads 52 and 54 or the like to form a closed container having a substantially annular chamber 56 bounded on the outside by the periphery of the container 12 and on the inside by a central pillar formed by the pillars 40 and 42.

In operation, the container 12 is filled with the required amount of water and the lid 38 is threaded into place to seal the container and form the annular chamber 56 which will be almost full of water (sufficient space will be provided to accommodate the expansion on freezing). This container 12 is then placed in a suitable cold spot such as a freezer to freeze the water and form an annular ring of ice surrounding the pillars 40 and 42.

While the contents of the container 12 are freezing the pockets 18 and 20 in the wall 14 of the insulated container 10 may be charged with the required equipment such as the swabs and syringes 22. The number of such pockets may be correlated with the size of the containers 10 and 12 and the degree of insulation of the outer container 10 and lid 32 to provide the equipment that may be required for the time period the insulin will be safely stored in the cooler.

After the content of the container 12 has frozen (preferably water but other material may be used to provide the cooling) the container 12 is slid into the cavity 24 in outer container 10, the insulin containing bottle 50 is place into the compartment 48 and the lid 32 screwed into position so that the insulation 34 closes the cavity 24 and insulates the container 12 from the atmosphere while the flange 36 covers the pockets 18 and 20 and prevents the contents from falling out.

The insulin may be stored in such a case for days assuming sufficient insulation in the outer container 10. The shape of the closed inner container 12 ensures optimum temperature control of the insulin as illustrated in FIG. 6 by surrounding the insulin with a ring of ice. As the water melts, the ice remains afloat at the top and in close contact with the cavity 48 in which the insulin bottle 50 is contained. It will also be noted that the amount of coolant surrounding the insulin bottle 50 is so significantly larger than the size of the insulin bottle 50, periodic removal of the insulin bottle for use does not appreciably affect the efficiency of the device.

When one is ready to use the insulin, the top 32 is removed, a syringe extracted from one of the pockets 18, and a swab from one of the pockets 20, the area to be injected prepared and the syringe charged with insulin in the conventional manner and in any event the lid 32 is replaced to seal the container 10 as soon as possible, either before or after the insulin has been injected. The used syringe is then disposed of.

FIG. 6 indicates the time/temperature curve for a cooler constructed as illustrated and having insulated walls 14 and 16 formed of 1½ inch foam urethane and the inner container 12 containing 28 ounces of ice. Clearly the insulin was held at about 36° F. for a period of about 70 hours.

Modification may be made without departing from the spirit of the invention as defined in the appended claims.

I claim:

1. A cooler comprising an outer container having insulated peripheral and bottom walls defining a cavity, an insulated lid for closing said cavity, an inner container adapted to be received within said cavity, a top closure for said inner container, said inner container and said top closure combining when said top closure is in place closing said inner container to form a substantially annular closed cooling medium chamber surrounding an inner central pillar, said pillar providing a top opening compartment adapted to receive material for storage, opposite inner side walls of said annular closed cooling medium chamber being spaced so that when a solid ring of ice is contained in said cooling medium chamber it floats to the top of water in said cooling medium chamber.

2. A cooler as defined in claim 1 wherein said central pillar is formed by an upwardly extending pillar and a downwardly extending pillar projecting from a bottom wall of said inner container and said top closure respectively, said downward extending pillar forming said top opening compartment.

3. A cooler as defined in claim 1 wherein said peripheral wall is provided with a plurality of pockets and wherein said lid is removable and is provided with means for closing said pockets when said lid is in position, closing said cavity.

4. A cooler as defined in claim 2 wherein said peripheral wall is provided with a plurality of pockets and wherein said lid is removable and is provided with means for closing said pockets when said lid is in position, closing said cavity.

5. A cooler as defined in claims 3 or 4 specially adapted as an insulin travel kit further comprising an insulin bottle in said compartment and disposable syringes in at least some of said pockets, said annular chamber being substantially full of cooling medium.

* * * * *